(12) United States Patent
Richard

(10) Patent No.: US 10,004,570 B2
(45) Date of Patent: Jun. 26, 2018

(54) ASSEMBLY COMPRISING A COMPONENT AND AN AXIAL LIMIT STOP DEVICE INTENDED TO BE PLACED IN A BORE OF SAID COMPONENT

(71) Applicant: ANTHOGYR, Sallanches (FR)

(72) Inventor: Hervé Richard, Notre Dame de Bellecombe (FR)

(73) Assignee: ANTHOGYR, Sallanches (FR)

( * ) Notice: Subject to any disclaimer, the term of this patent is extended or adjusted under 35 U.S.C. 154(b) by 79 days.

(21) Appl. No.: 15/066,158

(22) Filed: Mar. 10, 2016

(65) Prior Publication Data

US 2016/0270877 A1 Sep. 22, 2016

(30) Foreign Application Priority Data

Mar. 17, 2015 (FR) ...................................... 15 52206
Jul. 3, 2015 (FR) ...................................... 15 56332

(51) Int. Cl.
*A61C 1/08* (2006.01)
*F16B 39/24* (2006.01)
(Continued)

(52) U.S. Cl.
CPC ............ *A61C 1/084* (2013.01); *A61C 8/0022* (2013.01); *A61C 8/0089* (2013.01); *F16B 39/24* (2013.01); *F16B 41/002* (2013.01)

(58) Field of Classification Search
CPC ..... A61C 1/084; A61C 8/0022; A61C 8/0059; F16B 39/24; F16B 41/002
See application file for complete search history.

(56) References Cited

U.S. PATENT DOCUMENTS 2,766,799 A * 10/1956 Poupitch ................. F16B 39/24
411/134
3,054,436 A * 9/1962 Rosan ................... F16B 37/122
411/109

(Continued)

FOREIGN PATENT DOCUMENTS

EP 0801544 B1 12/1998
EP 1060716 A2 12/2000
WO 2012037014 A2 3/2012

*Primary Examiner* — Nicholas Lucchesi
(74) *Attorney, Agent, or Firm* — William H. Eilberg

(57) ABSTRACT

Assembly including a component and a one-piece axial limit stop device intended to be placed in a bore of said component in order to retain an element therein, including an annular ring with symmetry of revolution about a central axis (I-I), and including at least one angular portion rigidly connected to the annular ring, developing in an arc between a first end, joined to the distal end of the annular ring, and a second, free end. The angular portion is in part movable from its first end, in a transverse plane perpendicular to the central axis (I-I), between a retracted position and at least one protruding position, being elastically returned permanently to the protruding position. In the retracted position, the angular portion is included within the volume of a cylinder continuing the outer cylindrical surface of the annular ring. In the protruding position, the free end of the angular portion extends radially beyond the volume of the cylinder continuing the outer cylindrical surface of the annular ring. The component bore has a specific inner geometry allowing the axial limit stop device to be easily attached and reliably fixed, while at the same time allowing easy detachment and extraction of the axial limit stop device in order to permit the removal of the element in the event of the latter sustaining damage.

9 Claims, 13 Drawing Sheets

(51) Int. Cl.
*A61C 8/00* (2006.01)
*F16B 41/00* (2006.01)

(56) References Cited

U.S. PATENT DOCUMENTS

| | | | |
|---|---|---|---|
| 4,844,677 A * | 7/1989 | Schwartzman | F16B 39/24 |
| | | | 188/67 |
| 5,947,733 A | 9/1999 | Sutter | |
| 6,090,146 A | 7/2000 | Rozow | |
| 2007/0280802 A1* | 12/2007 | Disantis | F16B 35/041 |
| | | | 411/160 |
| 2012/0063864 A1* | 3/2012 | Hess | F16B 39/24 |
| | | | 411/326 |
| 2013/0266395 A1* | 10/2013 | Schuster | F16B 39/24 |
| | | | 411/216 |
| 2014/0273584 A1* | 9/2014 | Sun | H01R 13/622 |
| | | | 439/319 |
| 2014/0308089 A1 | 10/2014 | Hess | |
| 2017/0122361 A1* | 5/2017 | Davis | F16B 39/24 |

\* cited by examiner

ASSEMBLY COMPRISING A COMPONENT AND AN AXIAL LIMIT STOP DEVICE INTENDED TO BE PLACED IN A BORE OF SAID COMPONENT

TECHNICAL FIELD OF THE INVENTION

The present invention relates to an assembly comprising a component and an axial limit stop device intended to be placed in a bore of said component in order to retain an element therein. The field of use of the invention is in particular the field of dentistry, the aim being to retain a transfixing screw in a bore of a dental prosthesis that is intended to be attached to a dental implant.

The document EP 0 801 544 discloses a dental abutment intended to be attached to and fixed on a dental implant, which is itself intended to be inserted into the maxillary or mandibular bone of a patient. The dental abutment subsequently receives a final dental prosthesis made of ceramic or metal. The dental abutment has a continuous bore in which an axial limit stop device is arranged, which is intended to ensure the axial retention of a screw held captive in the bore of the abutment. The threaded shank portion of the screw is intended to be received by screwing in an internally threaded bore of the dental implant. The dental abutment is fixed to the dental implant by fixing means (specifically a screw) passing through the dental abutment, hence the expression "transfixed dental abutment", and more generally "transfixed component". The axial limit stop device has a radially slit ring, which simultaneously engages under the screw head and in an annular groove formed in the bore extending through the abutment.

In the event of an excessive screwing torque being imparted to the screw, the latter may sustain damage, especially by breaking in the area of its shank. It is then desirable to remove what remains of the screw in the continuous bore of the abutment, in order to be able to insert a new screw there. However, the slit ring of document EP 0 801 544 is unfortunately very difficult or even impossible to remove, mainly on account of the very small dimensions of the components in question (dental abutment and slit ring). Thus, any damage to the screw renders the dental abutment unusable. The practitioner is then compelled to use a new dental abutment provided with an intact screw.

Resorting to a new dental abutment is not in itself a great inconvenience, since it is a component of which the shape is not adapted to each patient and of which the practitioner has several models. A standard and rapid exchange is thus possible.

For many years, it has been sought to limit the number of components by managing without dental abutments for attaching and fixing a final dental prosthesis to a dental implant inserted in the maxillary or mandibular bone of a patient. To do so, it has been proposed to insert the screw directly into a bore formed in the final dental prosthesis. The fixing screw can be driven in rotation by means of a screwing tool which accesses the screw head by way of an access well that communicates with the bore (in most cases obliquely intersecting the bore) in which the screw is retained. These dental prostheses are often called "transfixed dental prostheses" since the screwing tool and the screw pass right through them when they are being fixed. However, in the event of damage to the screw, in the same way as has been described above for the dental abutment, it is likewise impossible for what remains of the screw to be removed from the bore. The damage to the screw thus renders the final prosthesis unusable. However, the outer shape of the final prosthesis is configured uniquely for each patient, by a process that is often lengthy and difficult. The practitioner is then compelled to manufacture a new final dental prosthesis, which takes a lot of time and is expensive.

This problem is even more critical in the case of transfixed multiple dental prostheses that are intended to be received on a plurality of dental implants and, for this purpose, have a plurality of captive screws: damage to one of the screws can render the whole prosthesis unusable.

The document WO 2012/037014 A2 describes an annular ring with symmetry of revolution about a central axis, comprising two angular arc portions with respective free ends which are radially movable, in a transverse plane perpendicular to the central axis, between a retracted position and at least one protruding position, being elastically returned permanently to the protruding position. This annular ring is used to form a ratchet-type locking nut being placed in the bore of a washer. When the annular ring is received in the bore of the washer, optional tongues attached by welding allow the assembled annular ring to be retained definitively in the washer. To do so, the tongues bear permanently under the annular ring and oppose any removal of the ring from the washer by translation, and they do this irrespective of the rotation position of the annular ring with respect to the washer.

The document EP 1 060 716 A2 describes an axially compressible locking nut used in an orthopedic implant in the form of a prosthetic femoral stem.

SUMMARY OF THE INVENTION

A problem addressed by the present invention is to make available an assembly comprising a component and an axial limit stop device intended to be placed in a bore of said component in order to reliably retain an element therein, but with the axial limit stop device being able to be detached easily in order to permit the removal of the element in the event of the latter sustaining damage.

According to another aspect, the present invention aims to make available an assembly comprising a component and an axial limit stop device intended to be mounted removably in a bore of said component, said component having very small dimensions, as in the case of a dental prosthesis in particular.

To achieve these objects and others, the invention proposes an assembly according to claim 1.

When said at least one angular portion of the axial limit stop device is in the retracted position, the axial limit stop device can be inserted by a simple movement of axial translation, along the first longitudinal axis and in the direction of the distal end of the component bore, into the first portion of the component bore. Then, by driving the axial limit stop device a little farther into the component bore in the direction of the distal end of the component bore, said at least one angular portion can penetrate into the second component bore portion and come into line with the retaining seat of the second component bore portion and engage there in the protruding position by elastic return. If an attempt is made to extract the axial limit stop device from the bore, by an axial translation movement along the first longitudinal axis and in the direction of the inlet orifice of the component bore, said at least one angular portion comes to bear against the proximal retaining face of the retaining seat and opposes this extraction. The axial limit stop device is thus able to hold an element (such as a screw and screw head) captive in the bore.

In the case where the element retained in the bore is damaged and must be withdrawn from the component, it is still possible to extract the axial limit stop device from the bore despite everything. To do so, the axial limit stop device is turned about the first longitudinal axis of the bore in such a way as to bring said at least one angular portion against the angular part of the lateral surface of the second component bore portion, which extends in the continuation of the cylindrical lateral surface of the first component bore portion. Said at least one angular portion is thus brought back to the retracted position, such that the axial limit stop device can then be extracted from the component bore, via the first component bore portion, by a simple movement of axial translation along the first longitudinal axis and in the direction of the inlet orifice of the component bore.

Advantageously, said at least one angular portion can be kept apart from the distal end of the annular ring, along the central axis, by a spacer extending parallel to the central axis. The elastic return of the angular portion to the protruding position is therefore not disturbed by the angular portion rubbing against the distal end of the annular ring.

Preferably, perpendicular to the central axis, said at least one angular portion can have a thickness that decreases from its first end toward its second free end. This effectively limits the stresses induced in the area of connection between the spacer and the angular portion by a flexion of the angular portion bringing the latter back to the retracted position. If these stresses were too high, they could end up breaking the arm and/or the angular portion near their connection, especially in the case of an axial limit stop device of small dimensions.

An indentation, allowing the annular ring to be driven in rotation about the central axis, can advantageously be formed in a proximal end face of the annular ring. The proximal end of the annular ring is in fact the part of the axial limit stop device that is most easily accessible from outside of the component.

Preferably, the indentation can comprise two diametrically opposite notches. An indentation having symmetry makes it possible to more easily turn the axial limit stop device about its central axis.

Advantageously, the axial limit stop device can have two angular portions movable in the same transverse plane.

In the case of a plurality of angular portions, provision can preferably be made that:
the second component bore portion has a plurality of retaining seats,
each retaining seat is separated from the adjacent retaining seat by an angular part of the lateral surface of the second component bore portion which extends in the continuation of the cylindrical lateral surface of the first component bore portion.

Having two or more angular portions engaged in respective retaining seats makes it possible to better retain the axial limit stop device axially in the component.

The angular parts of the lateral surface of the second component bore portion, which extend in the continuation of the cylindrical lateral surface of the first component bore portion and which separate the adjacent retaining seats, allow all of the angular portions to be brought back simultaneously to the retracted position when the axial limit stop device is driven in rotation about the central axis.

The element intended to be placed in the bore of the component with the aid of the axial limit stop device can advantageously have:
a proximal portion of the element having a cross section with dimensions less than or equal to the internal diameter of the annular ring,
a distal portion with a cross section having at least one dimension greater than the internal diameter of the annular ring but less than or equal to the diameter of the first component bore portion,
a shoulder connecting the proximal portion and distal portion of the element.

The proximal portion of the element can thus pass through the axial limit stop device in order to protrude from the bore of the component, while the distal portion of the element bears axially along the shoulder against the axial limit stop device, in order to be retained in the bore of the component.

Preferably, the element intended to be placed in the cylindrical bore of the component can be a screw, of which the head constitutes the distal portion of the element and of which the threaded shank constitutes the proximal portion of the element.

To make it easier for the assembly according to the invention to be put together by inserting the axial limit stop device into the bore of the component, it is possible to use a mounting tool in which the following provisions can be made:
a tubular sleeve with a central bore extends along a second longitudinal axis between a distal orifice and a proximal orifice,
the central bore of the tubular sleeve has a tubular sleeve distal bore portion, extending from the distal orifice, a tubular sleeve intermediate bore portion, following on from the tubular sleeve distal bore portion and extending toward the proximal orifice, and a tubular sleeve proximal bore portion following on from the tubular sleeve intermediate bore portion and extending as far as the proximal orifice,
the tubular sleeve intermediate bore portion has a circular cross section with a diameter equal to or slightly greater than the external diameter of the annular ring,
the tubular sleeve distal bore portion has at least one retaining seat which extends radially with respect to the second longitudinal axis out from the volume of the cylinder continuing the cylindrical surface of the tubular sleeve intermediate bore portion, said retaining seat being able to receive said at least one angular portion of the axial limit stop device in the protruding position,
the retaining seat has a proximal retaining face extending along a transverse plane substantially perpendicular to the second longitudinal axis and connecting to the cylindrical lateral wall of the tubular sleeve intermediate bore portion,
the tubular sleeve distal bore portion has at least one angular part with a lateral surface extending in the continuation of the cylindrical lateral surface of the tubular sleeve intermediate bore portion.

A mounting tool of this kind proves particularly useful when the axial limit stop device has very small dimensions, as is especially the case when it is used to retain an element such as a screw in a dental prosthesis.

To insert the axial limit stop device into the bore of the component, it is first of all inserted into the tubular sleeve distal bore portion. Said at least one angular portion, then in the protruding position, is engaged in said at least one retaining seat provided in the tubular sleeve distal bore portion. By turning the axial limit stop device about the central axis, said at least one angular portion is then brought into line with said at least one angular part of the lateral surface extending in the continuation of the cylindrical lateral surface of the tubular sleeve proximal bore portion. The angular portion is thus brought back to the retracted position. The distal orifice of the tubular sleeve is then brought in immediate proximity to the inlet orifice of the component bore. The axial limit stop device, with its angular portion in the retracted position, is then pushed out of the tubular sleeve distal bore portion in order to be engaged in the first component bore portion until the angular portion of the axial limit stop device penetrates into the second component bore portion and comes into line with the retaining seat of the second component bore portion in order to engage there in the protruding position by elastic return.

To push the axial limit stop device out of the tubular sleeve distal bore portion, a longitudinal shaft can be passed through the tubular sleeve from the direction of the proximal orifice thereof.

The element intended to be retained in the component bore can be first engaged in the component bore before the axial limit stop device is engaged there. Alternatively, the element intended to be retained in the component bore can be introduced into the component bore at the same time as the axial limit stop device.

Preferably, provision can be made that:
the mounting tool has a longitudinal shaft extending along a third longitudinal axis, with a distal portion having an outer circular cross section of diameter substantially equal to the diameter of the tubular sleeve intermediate bore portion,
the distal portion of the longitudinal shaft extends along the third longitudinal axis by a length greater than the sum of the lengths of the tubular sleeve intermediate bore portion and tubular sleeve distal bore portion along the second longitudinal axis,
the distal portion of the longitudinal shaft has, at a free end, a distal face intended to bear against the proximal end of the annular ring,
the distal face of the distal portion of the longitudinal shaft has raised areas able to cooperate with the indentation formed in the face of the proximal end of the annular ring in order to drive the annular ring in rotation about its central axis.

The longitudinal shaft thus serves simultaneously:
to push the axial limit stop device out of the tubular sleeve distal bore portion in order to engage the axial limit stop device in the first component bore portion,
to turn the axial limit stop device about the central axis in the tubular sleeve distal bore portion in order to bring the angular portion to the retracted position.

BRIEF DESCRIPTION OF THE DRAWINGS

Other subjects, features and advantages of the present invention will become clear from the following description of particular embodiments, with reference being made to the attached figures in which.

DESCRIPTION OF THE PREFERRED EMBODIMENTS

Figure 8:
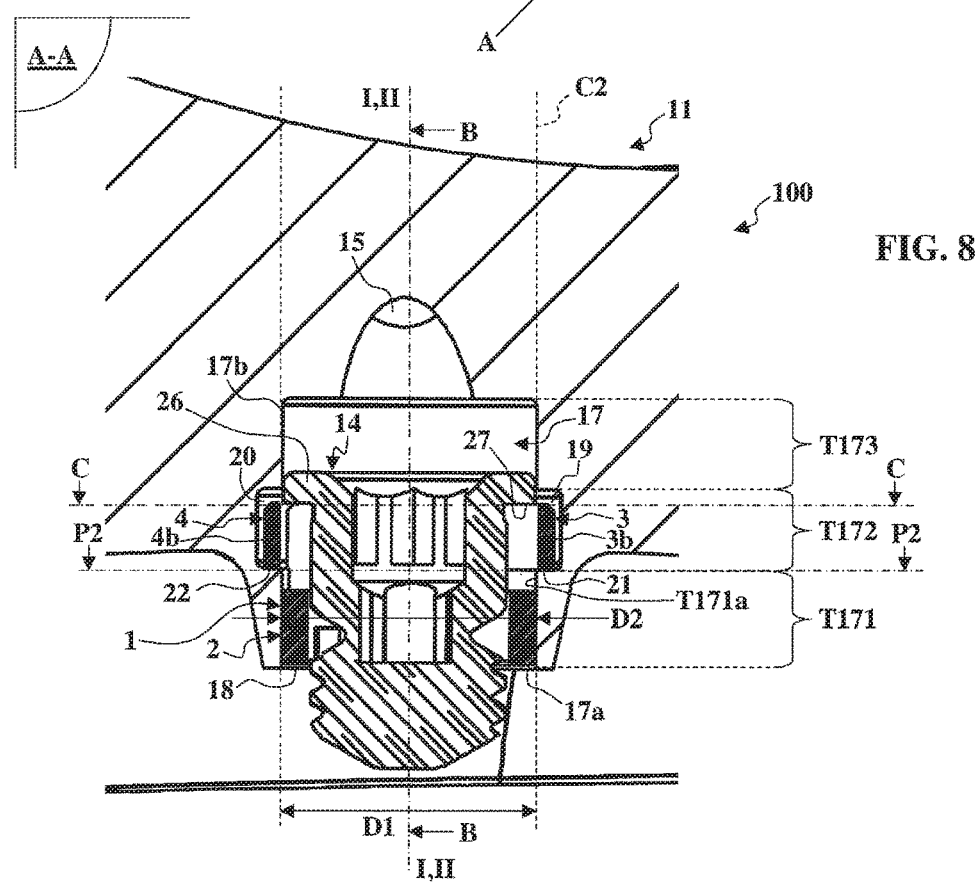
FIG. 8 is a detailed cross-sectional view, on a section plane A-A, of a particular embodiment of the assembly according to the invention, comprising the component from FIG. 6, in the form of a transfixed multiple dental prosthesis, in a bore of which an element is retained by the axial limit stop device of FIG. 1.
Figure 9:
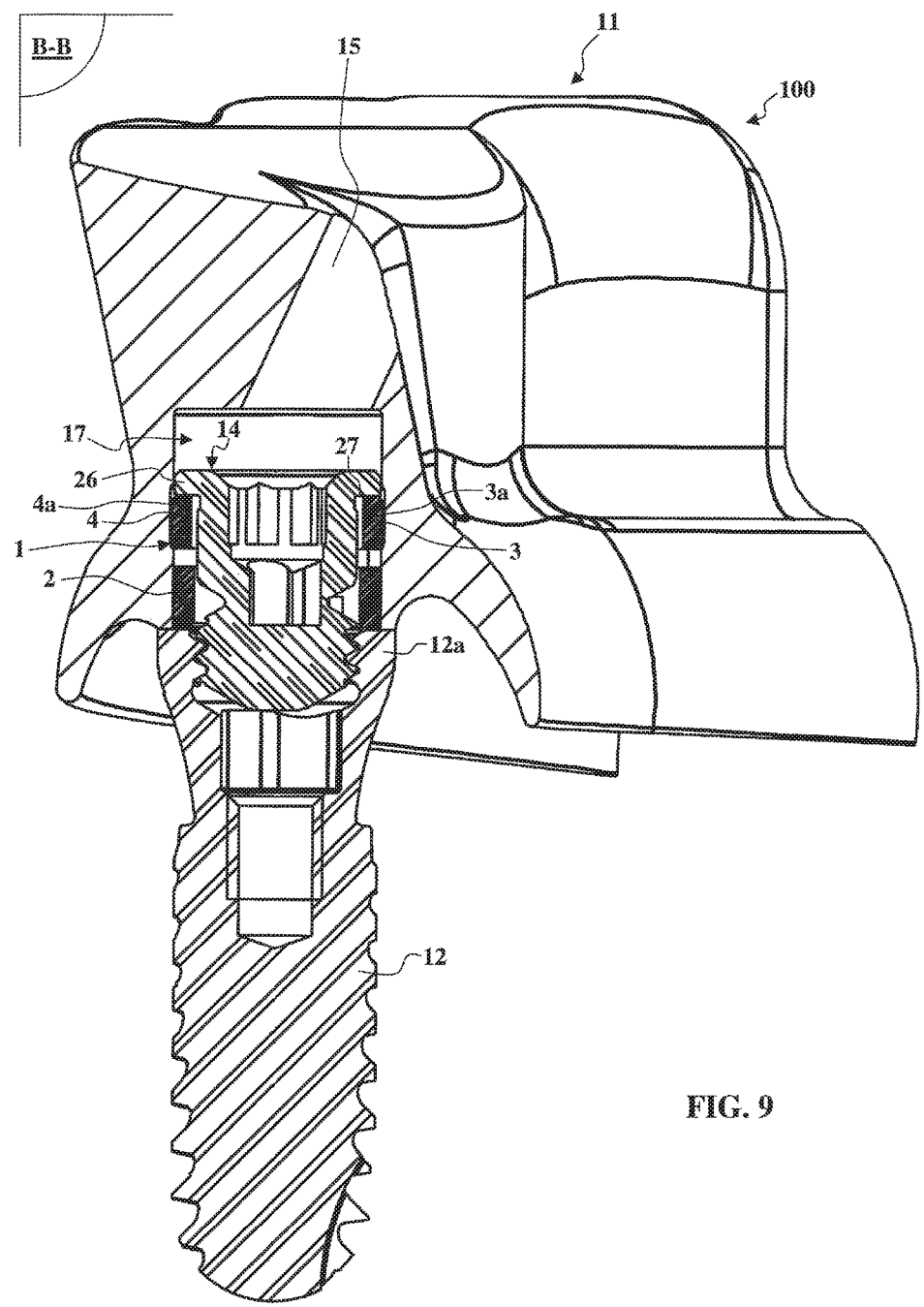
FIG. 9 is another detailed cross-sectional view of the assembly from FIG. 8, on a first variant of a dental implant, seen in a section plane B-B perpendicular to the section plane A-A of FIG. 8.
Figure 22:
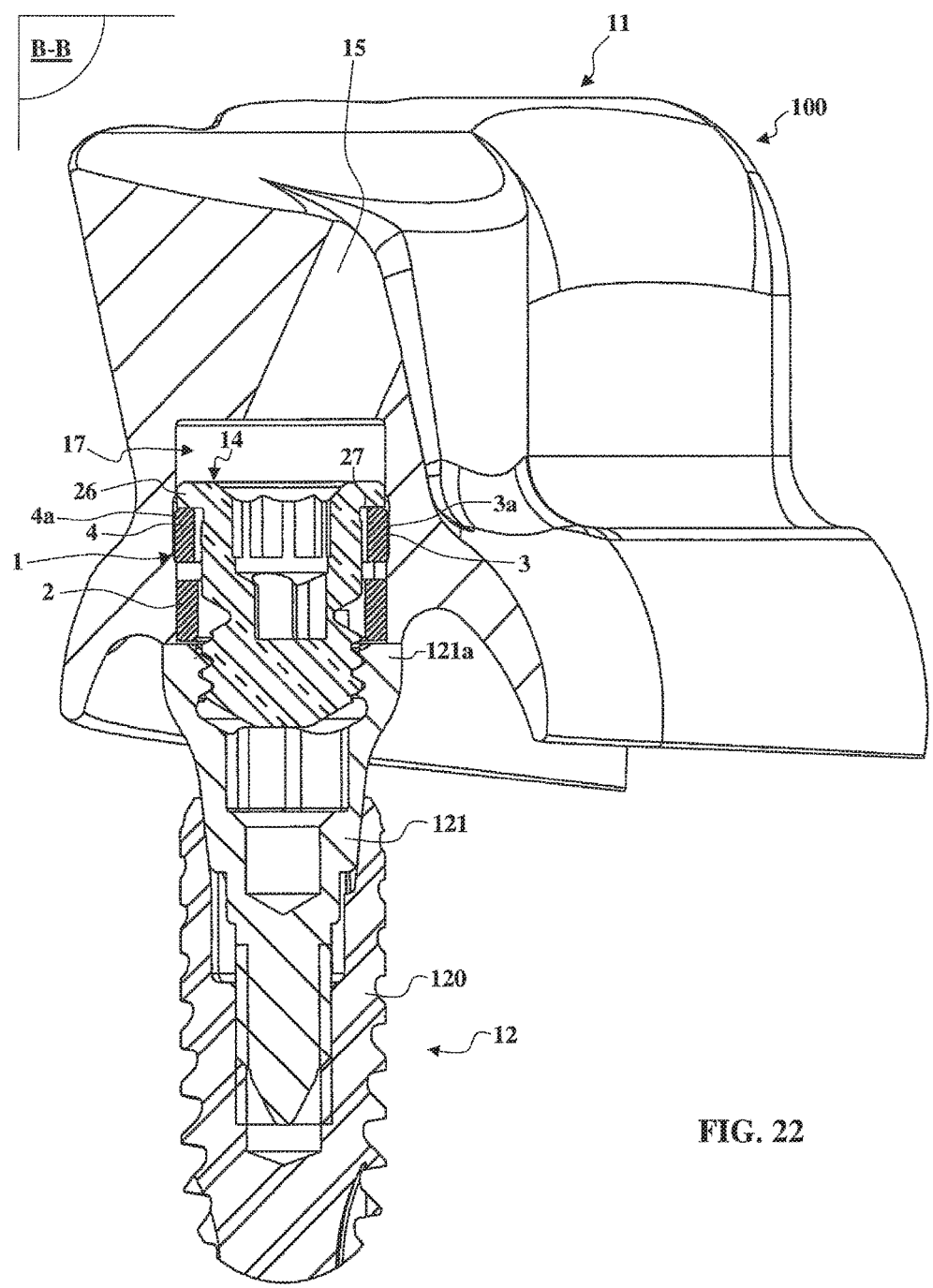
FIG. 22 is another detailed cross-sectional view of the assembly from FIG. 8, on a second variant of a dental implant, seen in a section plane B-B perpendicular to the section plane A-A of FIG. 8.

FIGS. 1 to 5 depict an example of an axial limit stop device 1 intended for the manufacture of a particular embodiment of an assembly 100 according to the invention (said assembly 100 can be seen more particularly in FIGS. 8, 9 and 22). The axial limit stop device 1 is in one piece and comprises an annular ring 2 which has symmetry of revolution about a central axis I-I and which extends along the central axis I-I between a proximal end 2a and a distal end 2b. Two angular portions 3 and 4 develop in an arc between first ends 3a and 4a, connected to the distal end 2b of the annular ring 2, and a second free end 3b and 4b. The angular portions 3 and 4 are in part radially movable by deformation, starting from their first ends 3a and 4a, in one and the same transverse plane P1 perpendicular to the central axis I-I, between a retracted position (illustrated in broken lines in FIG. 4) and at least one protruding position (illustrated in solid lines in FIGS. 1 to 5), by being elastically returned permanently to the protruding position.

Figure 4:
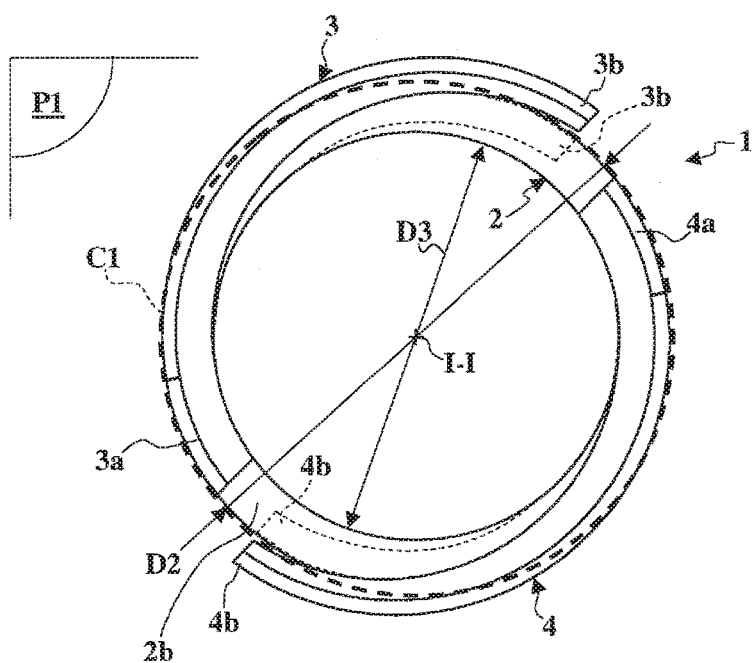
FIG. 4 is a top view of the axial limit stop device of FIG. 1.

As is illustrated in FIG. 4 in broken lines, in the retracted position, the angular portions 3 and 4 are included within the volume of a cylinder C1 continuing the outer cylindrical surface of the annular ring 2. In the protruding position, the free ends 3b and 4b of the angular portions 3 and 4 protrude beyond the volume of the cylinder C1 continuing the outer cylindrical surface of the annular ring 2.

Figure 1:
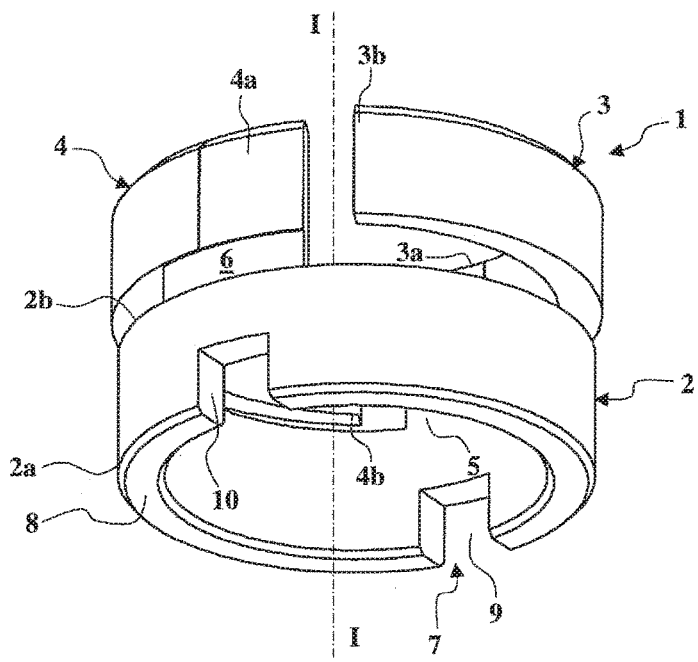
FIG. 1 is a perspective view of an example of an axial limit stop device intended to be used in a particular embodiment of the assembly according to the invention.
Figure 2:
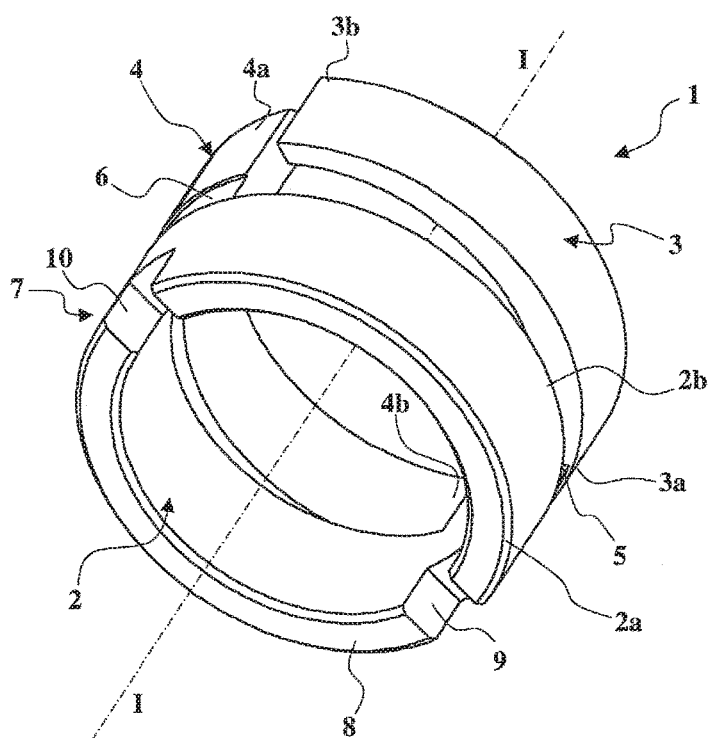
FIG. 2 is another perspective view of the axial limit stop device of FIG. 1, seen in a different direction from that of FIG. 1.

It will be seen more particularly in FIGS. 1 and 2 that the first ends 3a and 4a of the angular portions 3 and 4 and the distal end 2b of the annular ring 2 are connected by spacers 5 and 6 extending parallel to the central axis I-I. The angular portions 3 and 4 are thus kept apart from the distal end 2b of the annular ring 2 along the central axis I-I.

Figure 5:
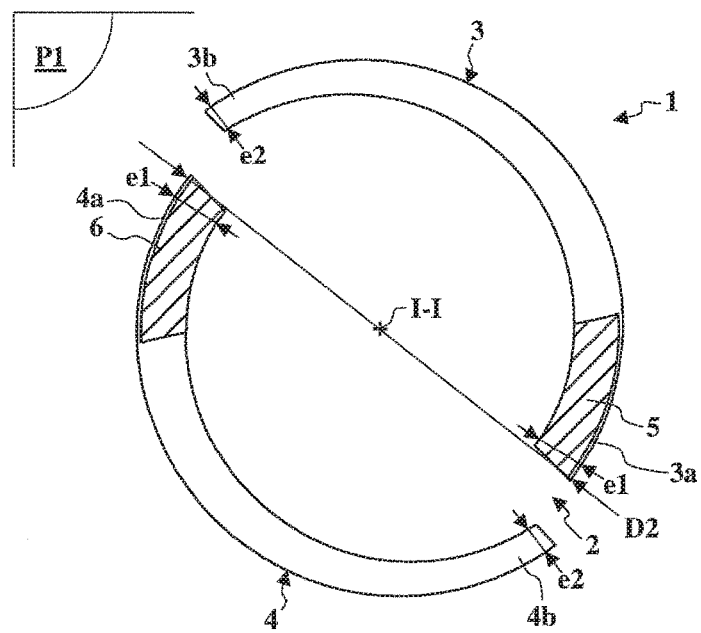
FIG. 5 is a bottom view, in cross section, of the axial limit stop device of FIG. 1.

It will be seen more particularly in FIG. 5 that, perpendicular to the central axis I-I, the angular portions 3 and 4 have a thickness which decreases from the first ends 3a and 4a toward the second free ends 3b and 4b. More precisely, the angular portions 3 and 4 have, near their first ends 3a and 4a, a radial thickness e1 that is greater than the radial thickness e2 near their second free ends 3b and 4b. The thickness of the angular portions 3 and 4 decreases progressively from e1 to e2.

Figure 3:
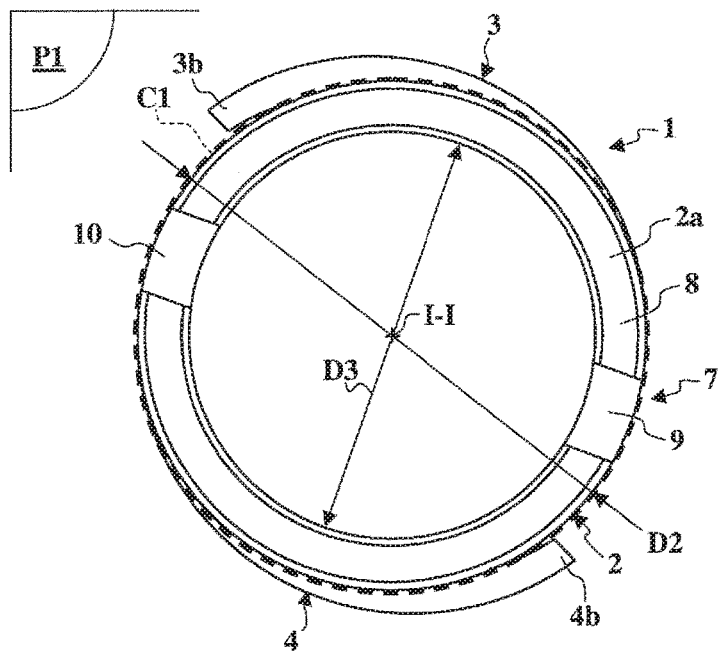
FIG. 3 is a bottom view of the axial limit stop device of FIG. 1.

It will be seen more particularly in FIGS. 1 to 3 that the axial limit stop device 1 comprises an indentation 7 for driving in rotation, allowing the annular ring 2 to be driven in rotation about the central axis I-I. This indentation 7 is formed in a face 8 of the proximal end 2a of the annular ring 2. In more detail, the indentation 7 has two diametrically opposite notches 9 and 10.

The axial limit stop device 1 in FIGS. 1 to 5 is intended to be placed in the bore of a component 11 in order to retain an element 14 therein.

Figure 6:
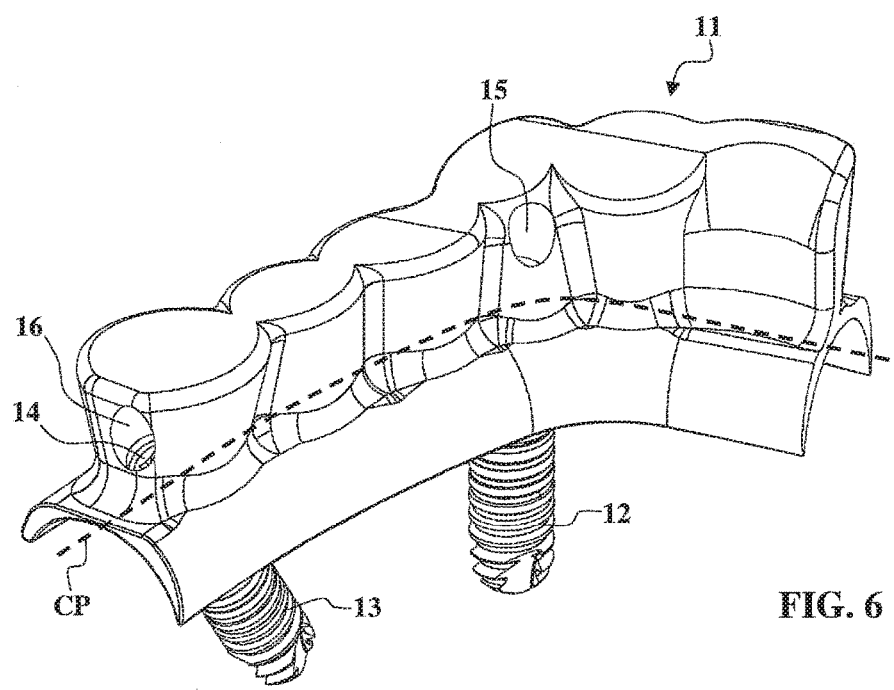
FIG. 6 is a perspective view of a component in the form of a transfixed multiple dental prosthesis, supported by a plurality of dental implants.
Figure 7:
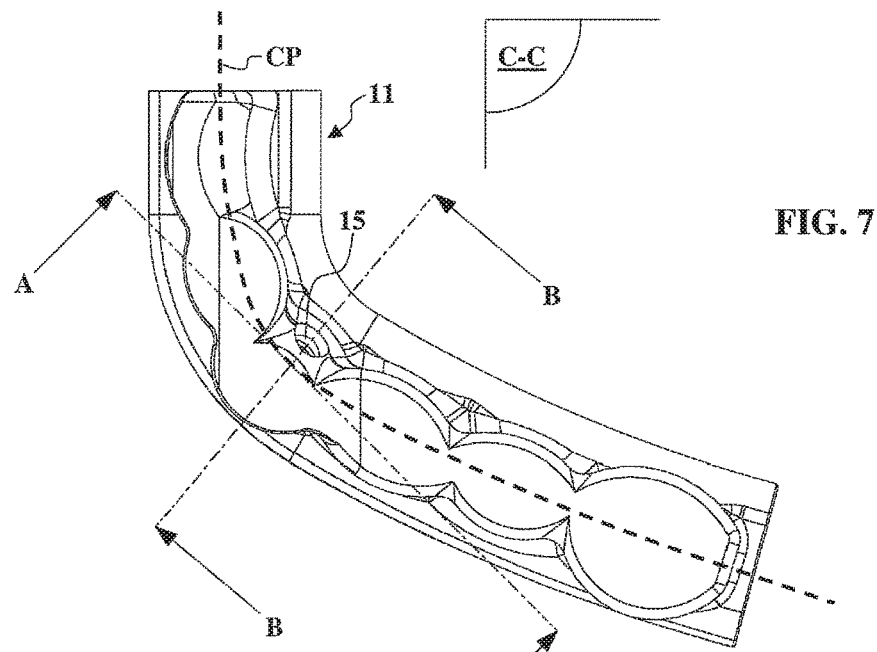
FIG. 7 is a top view of the transfixed multiple dental prosthesis of FIG. 6.
Figure 11:
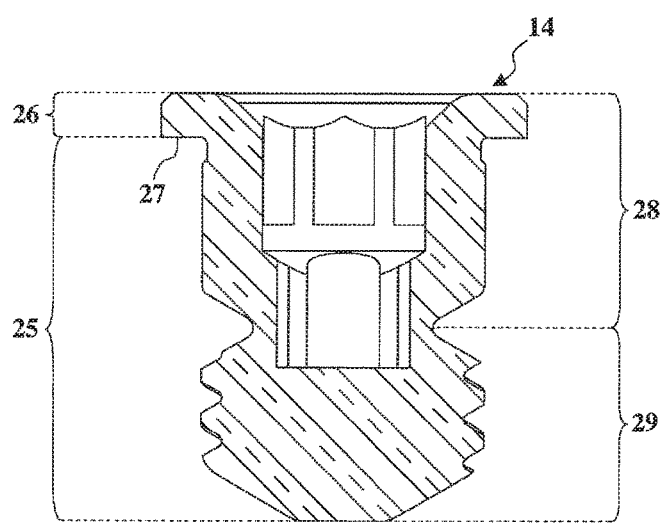
FIG. 11 is a cross-sectional side view of the element retained in the bore of the component, in the form of a transfixed multiple dental prosthesis, from FIGS. 8 and 9.
Figure 12:
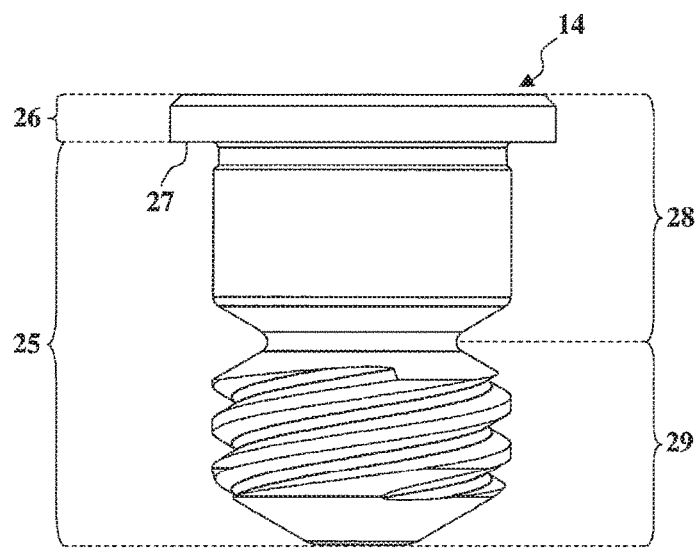
FIG. 12 is a side view of the element from FIG. 11.
Figure 13:
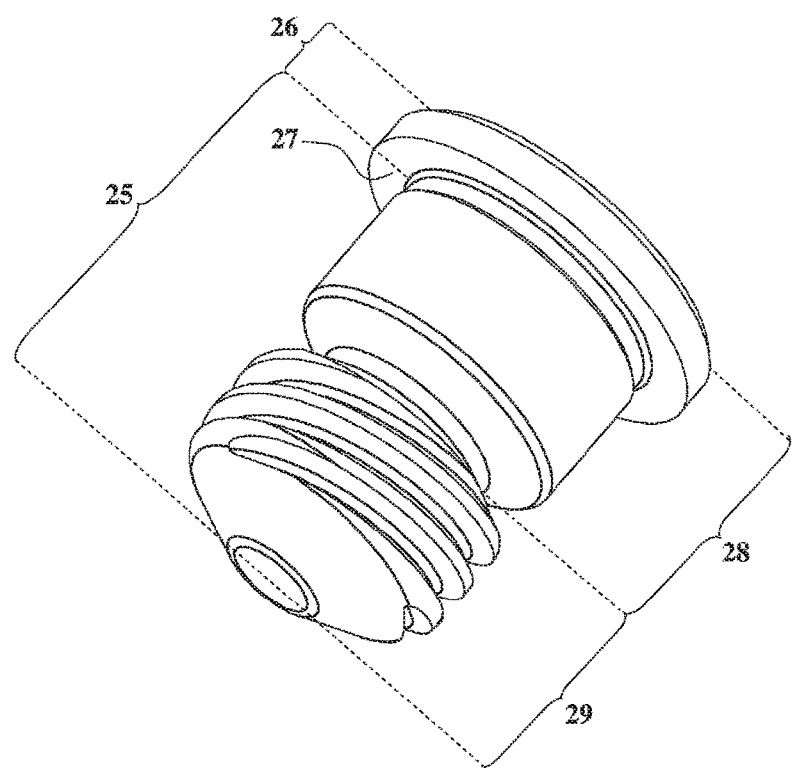
FIG. 13 is a perspective view of the element from FIG. 11.
Figure 14:
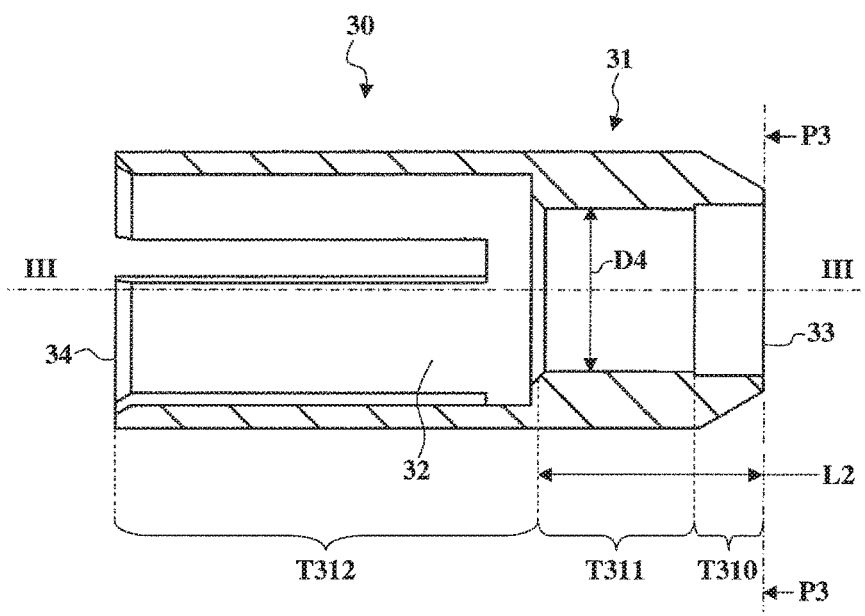
FIG. 14 is a cross-sectional view of a tubular sleeve of a mounting tool.
Figure 15:
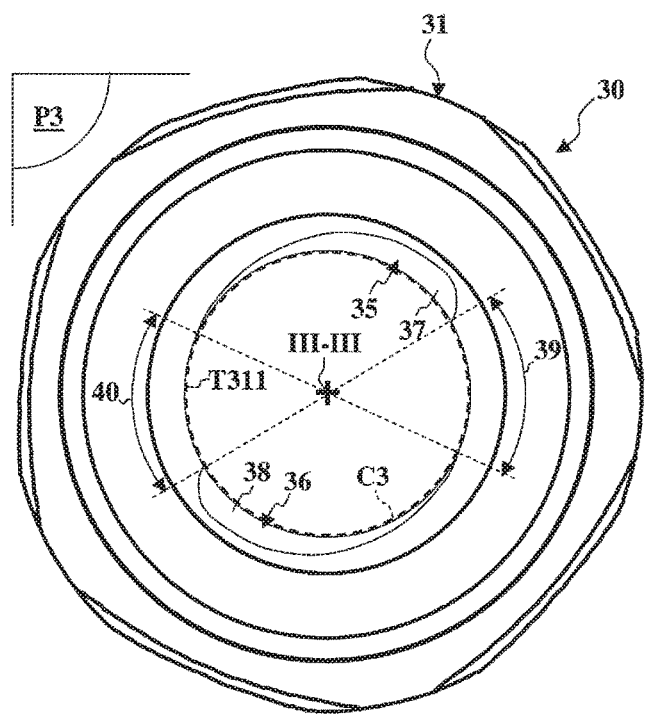
FIG. 15 is a view of the distal end of the tubular sleeve from FIG. 14.

In the field of dentistry, the axial limit stop device 1 is intended to be placed in a bore 17 formed in a component in the shape of a dental prosthesis 11, such as the transfixed multiple dental prosthesis 11 illustrated in FIGS. 6 and 7, in order to retain therein a screw 14 such as the one illustrated in FIGS. 11 to 13. The transfixed multiple dental prosthesis 11 extends in a plane C-C along a curved prosthetic corridor CP.

The transfixed multiple dental prosthesis 11 illustrated in FIGS. 6 and 7 is intended to be attached to and fixed on two dental implants 12 and 13, which are themselves intended to be received in the maxillary or mandibular bone of a patient. To do this, the transfixed multiple dental prosthesis 11 is fixed on the implants 12 and 13 by way of screws 14 such as those illustrated in FIGS. 11 to 13. The screws 14 are accessible by a screwing tool via access wells 15 and 16 which communicate with bores formed in the transfixed multiple dental prosthesis 11. This is revealed more particularly by FIGS. 8 and 9, which are cross-sectional views seen, respectively, along the section planes A-A and B-B illustrated in FIG. 7.

In FIGS. 8 and 9, it will be seen that the transfixed multiple dental prosthesis 11 has a bore 17 extending along a first longitudinal axis II-II between a proximal end 17a, with inlet orifice 18, and a distal end 17b. The axial limit stop device 1 is received in the component bore 17 with its central axis I-I coaxial with the first longitudinal axis II-II. The axial limit stop device 1 and the component 11, which is here in the form of a transfixed multiple dental prosthesis, form an assembly 100.

Said component bore 17 has a first component bore portion T171 extending from the inlet orifice 18 of the component bore 17, and a second component bore portion T172 following on from the first component bore portion T171 and extending toward the distal end 17b of the component bore 17. The component bore 17 additionally has a third component bore T173 following on from the second component bore portion T172 and extending as far as the distal end 17b of the component bore 17.

The first component bore portion T171 has a circular cross section with a diameter D1 equal to or slightly greater than the external diameter D2 of the annular ring 2.

The second component bore portion T172 has two retaining seats 19 and 20 which extend radially with respect to the first longitudinal axis II-II out from the volume of the cylinder C2 continuing the cylindrical surface of the first component bore portion T171. The retaining seats 19 and 20 are able to receive the angular portions 3 and 4 of the axial limit stop device 1 in the protruding position. The shape of the retaining seats 19 and 20 can be seen more particularly in FIG. 10, which is a cross-sectional view along the section plane C-C in FIG. 8.

Figure 10:
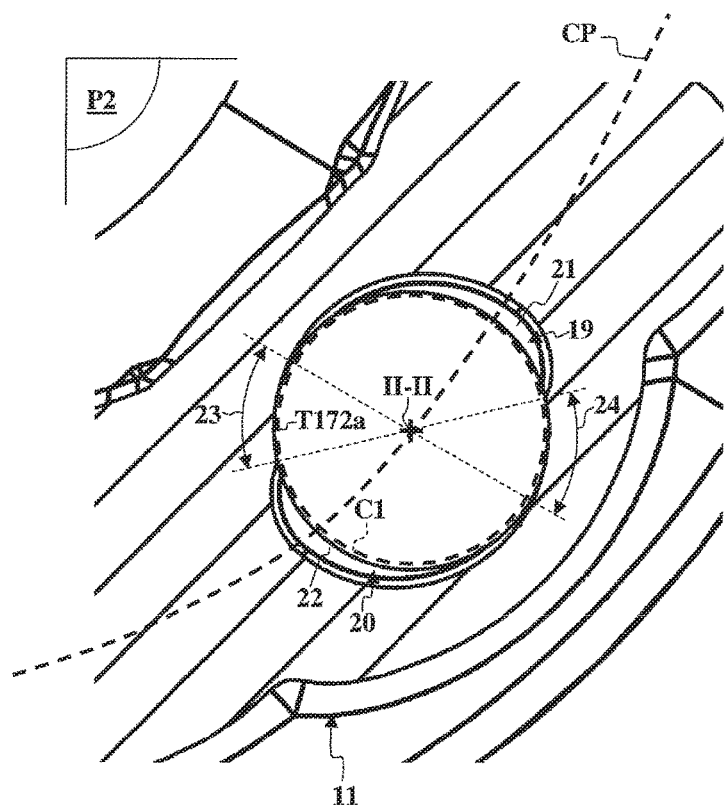
FIG. 10 is a detailed cross-sectional view of the bore of the component from FIG. 6, in the form of a transfixed multiple dental prosthesis, seen in a section plane C-C perpendicular to the section planes A-A and B-B of FIGS. 8 and 9.

In FIGS. 8 and 10, it will be seen that the retaining seats 19 and 20 have proximal retaining faces 21 and 22 extending along a transverse plane P2 substantially perpendicular to the first longitudinal axis II-II. In other words, the proximal retaining faces 21 and 22 extend in the transverse plane P2 substantially parallel to the section plane C-C illustrated in FIG. 8. The proximal retaining faces 21 and 22 are connected to the cylindrical lateral wall T171a of the first component bore portion T171.

The second component bore portion T172 has two angular parts 23 and 24 of the lateral surface T172a extending in the continuation of the cylindrical lateral surface T171a of the first component bore portion T171. The angular parts 23 and 24 are included within the diametric lines indicated by broken lines in FIG. 10. The angular parts 23 and 24 separate the adjacent retaining seats 19 and 20.

The retaining seats 19 and 20 develop radially with respect to the first longitudinal axis II-II and substantially along the prosthetic corridor CP. There is therefore more space available radially for drilling the retaining seats 19 and 20 and thereby increasing the axial retention of the axial limit stop device 1.

An element intended to be placed in the bore 17 of the component (transfixed multiple dental prosthesis 11) is illustrated more particularly in FIGS. 11 to 13. This element is a screw 14, and therefore it will be referred to below synonymously as element 14 or screw 14. The element 14 has:

- a proximal portion 25 with a cross section having dimensions less than or equal to the internal diameter D3 of the annular ring 2,
- a distal portion 26 with a cross section having at least one dimension greater than the internal diameter D3 of the annular ring 2 but less than or equal to the diameter D1 of the first component bore portion T171,
- a shoulder 27 joining the proximal portion 25 of the element and the distal portion 26 of the element.

As has already been explained, the element illustrated in FIGS. 11 to 13 is a screw 14, of which the head 28 comprises the distal portion 26 of the element, and of which the threaded shank 29 constitutes at least in part the proximal portion 25 of the element.

As is illustrated in FIGS. 8 and 9, when the axial limit stop device 1 is engaged in the bore 17 with its angular portions 3 and 4 engaged in the retaining seats 19 and 20 (FIG. 8), the distal element portion 26 of the screw 14 bears on the first ends 3a and 4a of the angular portions 3 and 4 along the shoulder 27. The axial bearing of the shoulder 27 against the first ends 3a and 4a and the axial bearing of the second free ends 3b and 4b against the proximal faces 21 and 22 allow the screw 14 to be retained axially in the bore 17 of the component, which is here represented by the transfixed multiple dental prosthesis 11.

The screw 14 can then be manipulated in turn, by driving it in rotation about the central axis I-I by means of a screwing tool engaged in the access well 15, in order to fix the transfixed multiple dental prosthesis 11 on the dental implant 12.

If the screw 14 has been damaged by application of an excessive rotational torque or by any other means, it is necessary that it can be extracted from the bore 17.

To do this, the axial limit stop device 1 is turned about the first longitudinal axis II-II (by means of the notches 9 and 10) in such a way as to bring the angular portions 3 and 4 against the angular parts 23 and 24 of the lateral surface T172a of the second component bore portion T172. The angular portions 3 and 4 are thus brought back to the retracted position, such that they no longer protrude radially in the retaining seats 19 and 20. The axial limit stop device 1 can then be extracted from the component bore 17, via the first component bore portion T171, by a simple movement of axial translation along the first longitudinal axis II-II and in the direction of the orifice 18 of the component bore 17.

FIGS. 14 to 17 illustrate a mounting tool 30 for mounting an axial limit stop device 1 in the bore 17 of the transfixed multiple dental prosthesis 11. As will be seen more particularly from FIGS. 14 and 15, the mounting tool 30 has a tubular sleeve 31 with a central bore 32 extending along a second longitudinal axis III-III between a distal orifice 33 and a proximal orifice 34. It will additionally be seen that:

the central bore 32 of the tubular sleeve 31 has a tubular sleeve distal bore portion T310 extending from the distal orifice 33, a tubular sleeve intermediate bore portion T311 following on from the tubular sleeve distal bore portion T310 and extending toward the proximal orifice 34, and a tubular sleeve proximal bore portion T312 following on from the tubular sleeve intermediate bore portion T311 and extending as far as the proximal orifice 34, the tubular sleeve intermediate bore portion T311 has a circular cross section of diameter D4 equal to or slightly greater than the external diameter D2 of the annular ring 2, the tubular sleeve distal bore portion T310 has two retaining seats 35 and 36 which extend radially with respect to the second longitudinal axis III-III out from the volume of the cylinder C3 continuing the cylindrical surface of the tubular sleeve intermediate bore portion T311, the retaining seats 35 and 36 being able to receive the angular portions 3 and 4 of the axial limit stop device 1 in the protruding position.

The retaining seats 35 and 36 each have a proximal retaining face 37 or 38, respectively, extending along a transverse plane P3 substantially perpendicular to the second longitudinal axis III-III and connecting to the cylindrical lateral wall of the tubular sleeve intermediate bore portion T311.

The tubular sleeve distal bore portion T310 has two angular parts 39 and 40 of the lateral surface extending in the continuation of the cylindrical lateral surface of the tubular sleeve intermediate bore portion T311. The angular parts 39 and 40 are included within the diametric lines indicated by broken lines in FIG. 15. Each retaining seat 35 and 36 is separated from the adjacent retaining seat 35 or 36 by an angular part 39 or 40.

Figure 16:
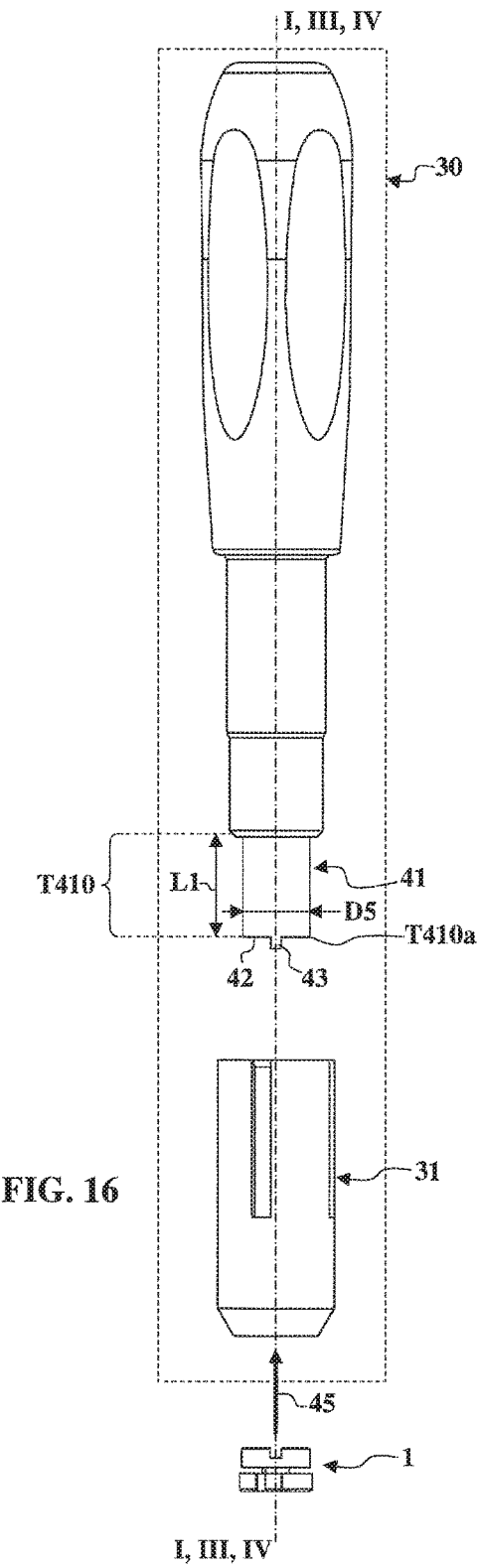
FIG. 16 is a side view of the tubular sleeve from FIG. 14, of an axial limit stop device from FIG. 1, and of a longitudinal shaft of the mounting tool.
Figure 17:
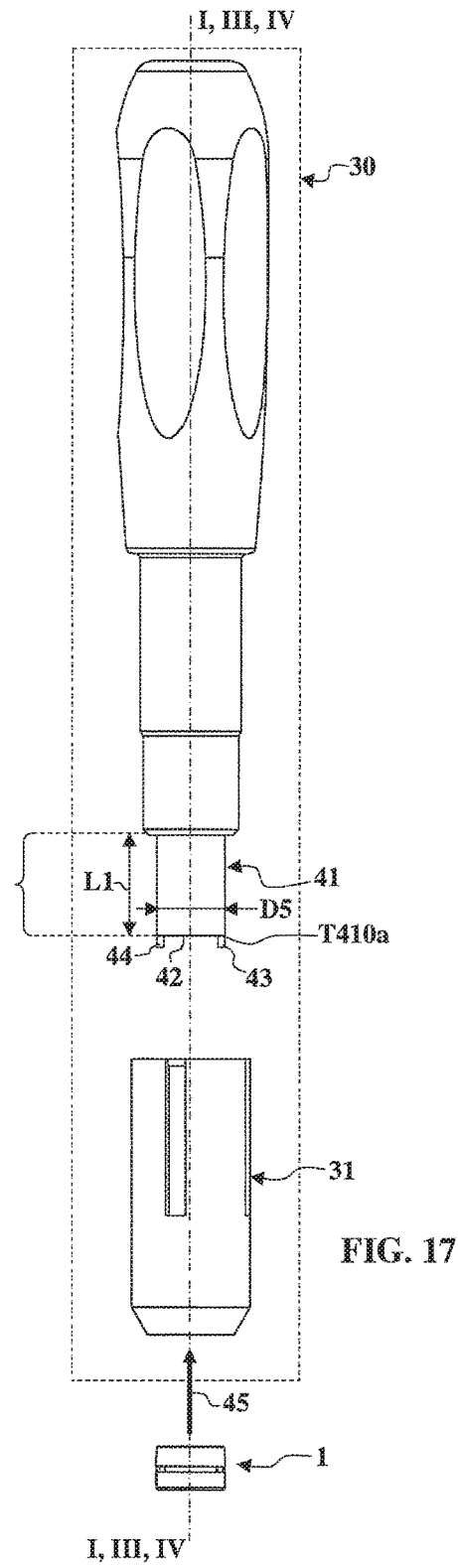
FIG. 17 is another side view of the elements of FIG. 16, seen in a direction perpendicular to that of FIG. 16.

It will be seen more particularly in FIGS. 16 and 17 that the mounting tool 30 likewise has a longitudinal shaft 41 extending along a third longitudinal axis IV-IV, with a distal portion T410 having a circular outer cross section of diameter D5 substantially equal to the diameter D4 of the tubular sleeve intermediate bore portion T311. The distal portion T410 of the longitudinal shaft extends along the third longitudinal axis IV-IV by a length L1 greater than the sum of the lengths (along the second longitudinal axis III-III) of the tubular sleeve intermediate bore portion T311 and of the tubular sleeve distal bore portion T310. The engagement of the distal portion T410 of the longitudinal shaft in the tubular sleeve intermediate bore portion T311 and the tubular sleeve distal bore portion T310 can thus eject from the tubular sleeve 31 an axial limit stop device 1 which would be inserted in the tubular sleeve distal bore portion T310.

To move the axial limit stop device 1 in rotation with respect to the tubular sleeve 31 about the second longitudinal axis III-III, it will be seen that:

the distal portion. T410 of the longitudinal shaft has, at a free end T410a, a distal face 42 intended to bear against the proximal end 2a of the annular ring 2, the distal face 42 of the distal portion T410 of the longitudinal shaft has raised areas, specifically two tongues 43 and 44, which are able to cooperate with the indentation 7 formed in the face 8 of the proximal end 2a of the annular ring 2 (by engaging in the notches 9 and 10) in order to drive the annular ring 2 in rotation about its central axis I-I with respect to the tubular sleeve 31. A use of the mounting tool 30 to insert and fix an axial limit stop device 1 in the bore 17 of a transfixed multiple dental prosthesis 11 will be explained below with the aid of FIGS. 16 to 21.

The axial limit stop device 1 is first of all inserted with a translation movement, illustrated by the arrow 45 in FIGS. 16 and 17, into the tubular sleeve distal bore portion T310. During this insertion, the angular portions 3 and 4, in the protruding position, are received in the retaining seats 35 and 36 while the annular ring 2 is received in the tubular sleeve intermediate bore portion T311.

Figure 18:
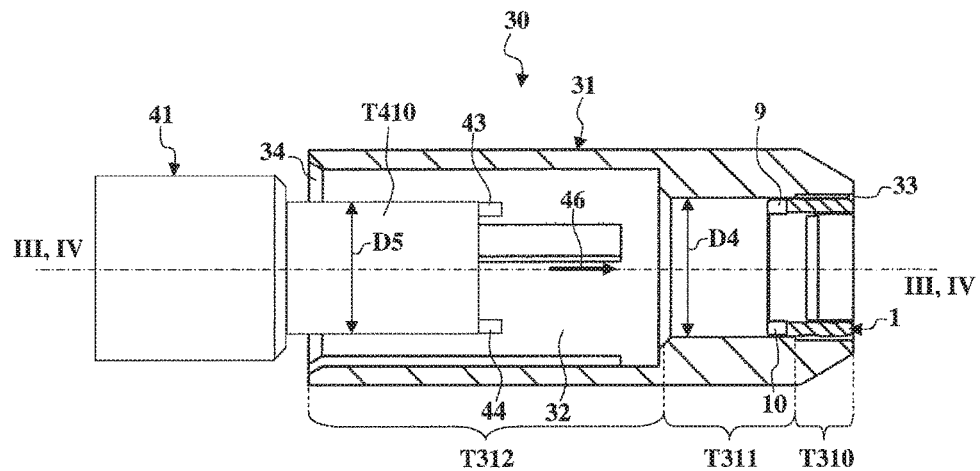
FIGS. 18 and 19 are detailed cross-sectional side views illustrating the cooperation of the elements of FIG. 16.
Figure 19:
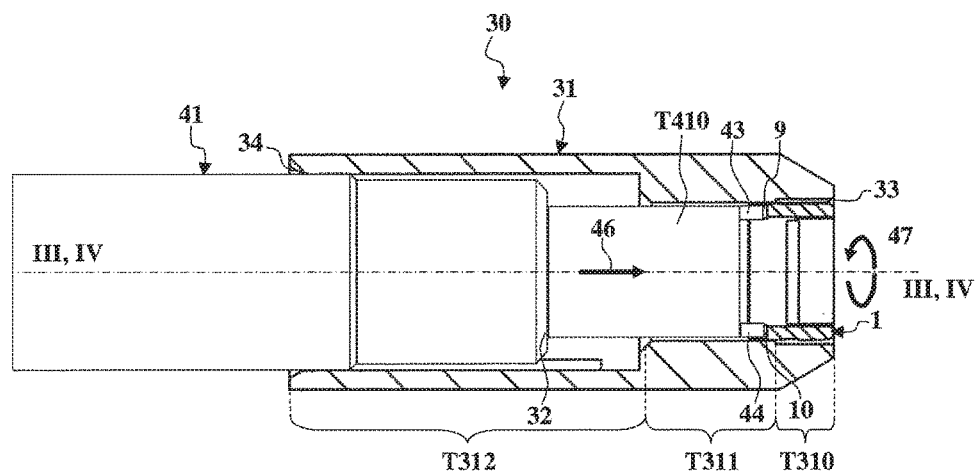

After this assembling of the tubular sleeve 31 and of the axial limit stop device 1, the longitudinal shaft 41 is inserted into the central bore 32 of the tubular sleeve 31 from the proximal orifice 34 toward the distal orifice 33, according to the movement illustrated by the arrow 46 in FIGS. 18 and 19.

The longitudinal shaft 41 is inserted into the central bore 32 until the tongues 43 and 44 engage in the notches 9 and 10, as is illustrated in FIG. 19.

The practitioner then moves the longitudinal shaft 41 in rotation about the second longitudinal axis III-III (coinciding with the central axis I-I and the third longitudinal axis IV-IV), in such a way as to bring the angular portions 3 and 4 into line with the angular parts 39 and 40 of the tubular sleeve distal bore portion T310 (movement illustrated by the arrow 47 in FIG. 19). The angular portions 3 and 4 are thus brought back to a retracted position.

Figure 20:
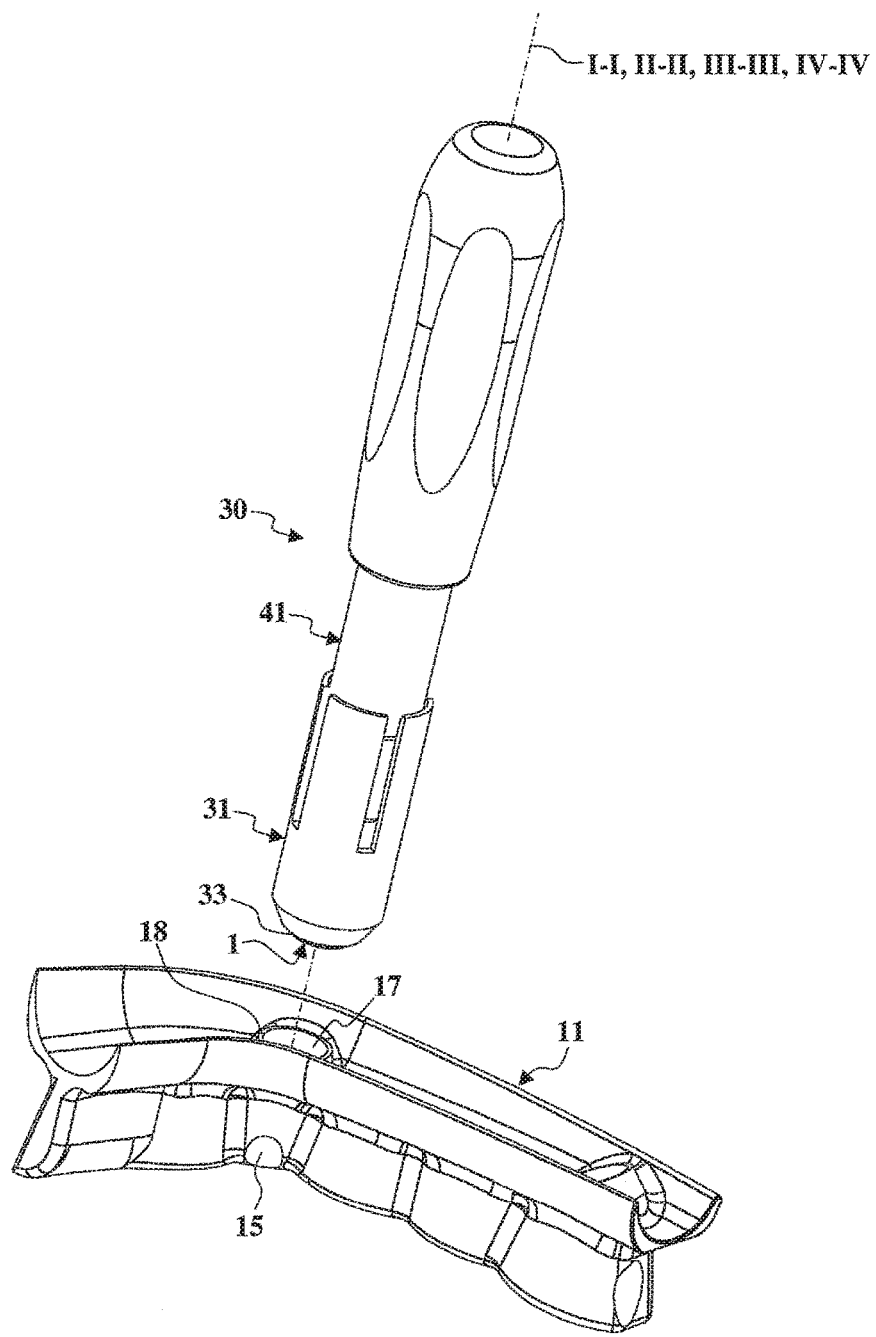
FIGS. 20 and 21 are perspective views illustrating the use of the tubular sleeve from FIG. 14 and of the longitudinal shaft from FIG. 16 for fitting an axial limit stop device from FIG. 1 in a bore of the component from FIG. 6, in the form of a transfixed multiple dental prosthesis.

The assembly formed by the axial limit stop device 1 (with its angular portions 3 and 4 in the retracted position), the tubular sleeve 31 and the longitudinal shaft 41 is then arranged with the central axis I-I, the second longitudinal axis III-III and the third longitudinal axis IV-IV coinciding with the first longitudinal axis II-II as illustrated in FIG. 20.

Figure 21:
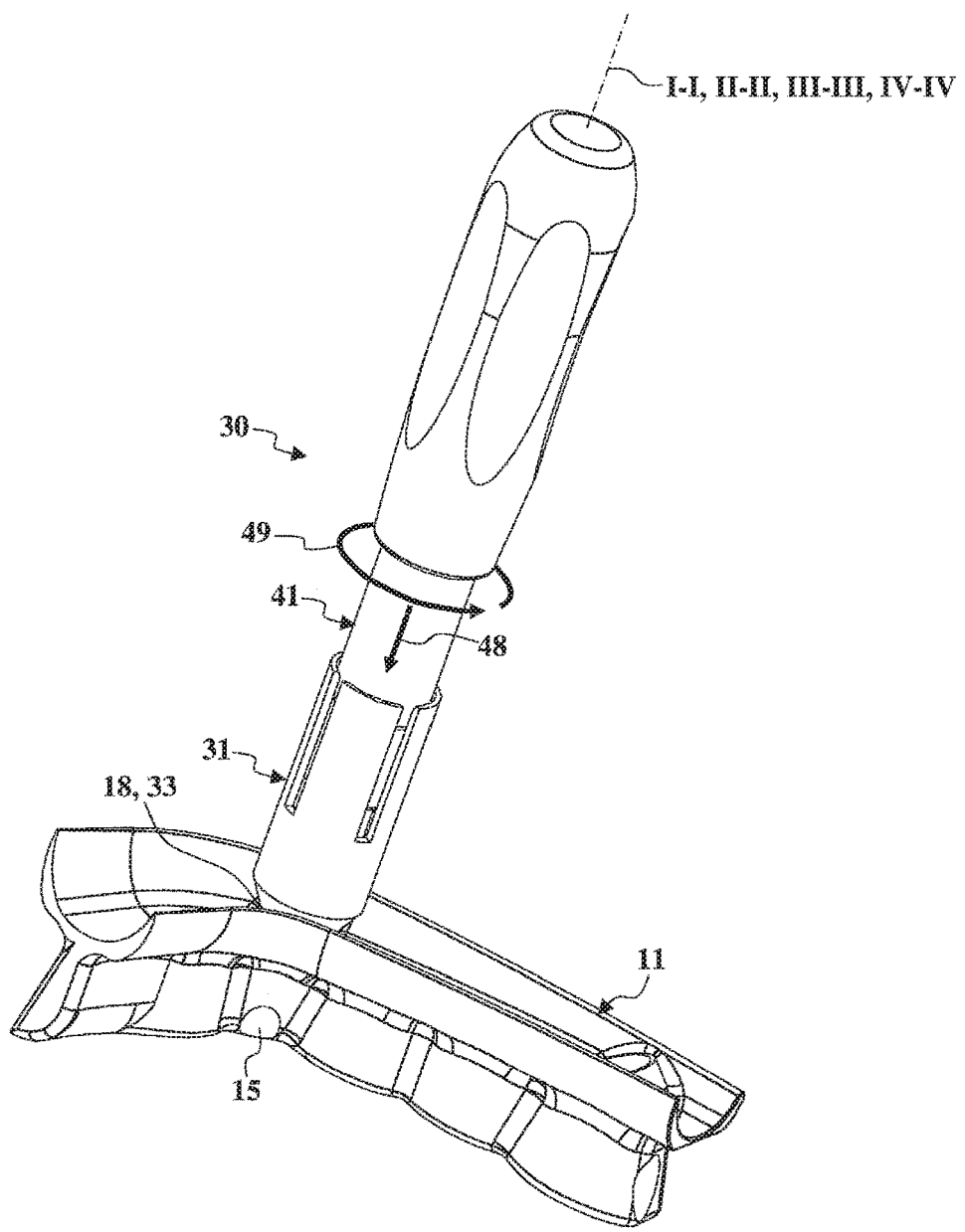

The assembly formed by the axial limit stop device 1, the tubular sleeve 31 and the longitudinal shaft 41 is then moved until the distal orifice 33 of the tubular sleeve 31 comes into contact with the inlet orifice 18 of the component bore 17 as illustrated in FIG. 21. The longitudinal shaft 41 is then moved with respect to the tubular sleeve 31 according to the axial translation movement illustrated by the arrow 48. The longitudinal shaft 41 then pushes the axial limit stop device 1 (with its angular portions 3 and 4 in the retracted position) through the first component bore portion T171 until the angular portions 3 and 4 come into line (axially) with the second component bore portion T172. At that moment, if the angular portions 3 and 4 are likewise located in line (radially) with the retaining seats 19 and 20, they are elastically returned to the protruding position and penetrate radially into the retaining seats 19 and 20. The axial limit stop device 1 is thus duly installed in the bore 17, as illustrated in FIGS. 8 and 9. In the case where the angular portions 3 and 4 are located in line with the angular parts 23 and 24 and thus remain in the retracted position in the second component bore portion T172, a rotation movement illustrated by the arrow 49 can be applied to the axial limit stop device 1 by the longitudinal shaft 41 in such a way as to bring the angular parts 3 and 4 into line with the retaining seats 19 and 20 and permit the movement of the angular portions to the protruding position.

The screw 14 can be installed in the bore 17 prior to the insertion of the axial limit stop device 1 into the bore 17. Alternatively, before the axial limit stop device 1 has been inserted into the tubular sleeve distal bore portion T310, it is also possible to insert the screw 14 through the axial limit stop device 1 until the shoulder 27 comes to bear on the angular portions 3 and 4. It is then the subassembly formed by the axial limit stop device 1 and the screw 14 that is simultaneously pushed axially into the bore 17 during the relative translation movement, illustrated by the arrow 48 in FIG. 21, between the tubular sleeve 31 and the longitudinal shaft 41.

To disassemble the axial limit stop device 1, the latter is moved in rotation about the central axis I-I until the angular portions 3 and 4 are brought back to the retracted position by cooperation with the angular parts 23 and 24 of the component bore 17. This can be accomplished by using the longitudinal shaft 41 and its tongues 43 and 44.

The axial limit stop device 1 (and the screw 14) can then be pushed in the direction of the inlet orifice 18 out of the bore 17 by a pusher tool (a rod for example) bearing against the axial limit stop device 1 (and/or the screw 14) by passing through the access well 15.

In a first variant illustrated in FIG. 9, the dental implant 12 is in just one piece, and its upper end 12*a* is intended to pass at least partially through the mucosa.

In a second variant illustrated in FIG. 22, the dental implant 12 is in two pieces, being composed of an osseous anchor 120 and of a transmucosal extension 121. The transmucosal extension 121 has an upper end 121*a* intended to pass at least partially through the mucosa.

The present invention is not limited to the embodiments that have been explicitly described, and instead it includes the different variants and generalizations contained within the scope of the attached claims.

The invention claimed is:

1. Assembly comprising a component and an axial limit stop device intended to be placed in a bore of said component in order to retain an element therein, in which:
    the axial limit stop device is in one piece and comprises an annular ring which has symmetry of revolution about a central axis (I-I) and which extends along the central axis (I-I) between a proximal end and a distal end,
    the axial limit stop device comprises at least one angular portion developing in an arc between a first end, joined to the distal end of the annular ring, and a second, free end,
    the at least one angular portion is in part movable radially from its first end, in a transverse plane (P1) perpendicular to the central axis (I-I), between a retracted position and at least one protruding position, being elastically returned permanently to the protruding position,
    in the retracted position, the at least one angular portion is included within the volume of a cylinder (C1) continuing an outer cylindrical surface of the annular ring,
    in the protruding position, the free end of the at least one angular portion extends radially beyond the volume of the cylinder (C1) continuing the outer cylindrical surface of the annular ring,
    said component bore extends along a first longitudinal axis (II-II) between a proximal end, with an inlet orifice, and a distal end and is intended to receive the axial limit stop device oriented with its central axis (I-I) coaxial to the first longitudinal axis (II-II),
wherein:
    said component bore comprises a first component bore portion extending from the inlet orifice of the component bore, a second component bore portion following on from the first component bore portion and extending toward the distal end of the component bore,
    the first component bore portion has a cylindrical lateral surface having a circular cross section with a diameter (D1) equal to or slightly greater than the external diameter (D2) of the annular ring,
    the second component bore portion has at least one retaining seat which extends radially with respect to the first longitudinal axis (II-II) out from the volume of a cylinder (C2) continuing the cylindrical lateral surface of the first component bore portion, said at least one retaining seat being able to receive said at least one angular portion of the axial limit stop device in the protruding position,
    the at least one retaining seat has a proximal retaining face extending along a transverse plane (P2) substantially perpendicular to the first longitudinal axis (II-II) and connecting to the cylindrical lateral surface of the first component bore portion,
    the second component bore portion has at least one angular part of its lateral surface which extends in the continuation of the cylindrical lateral surface of the first component bore portion.

2. Assembly according to claim 1, wherein said at least one angular portion is kept apart from the distal end of the annular ring, along the central axis (I-I), by a spacer extending parallel to the central axis (I-I).

3. Assembly according to claim 1, wherein, perpendicular to the central axis (I-I), said at least one angular portion has a thickness that decreases from its first end toward its second, free end.

4. Assembly according to claim 1, comprising an indentation, allowing the annular ring to be driven in rotation about the central axis, (I-I), and formed in a face of the proximal end of the annular ring.

5. Assembly according to claim 4, wherein the indentation has two diametrically opposite notches.

6. Assembly according to claim 1, wherein the axial limit stop device has two angular portions movable in the same transverse plane (P1).

7. Assembly according to claim 1, wherein:
the second component bore portion has a plurality of retaining seats,
each retaining seat is separated from the adjacent retaining seat by an angular part of the lateral surface of the second component bore portion which extends in the continuation of the cylindrical lateral surface of the first component bore portion.

8. Assembly according to claim 1, wherein the component is a transfixed multiple dental prosthesis.

9. Assembly according to claim 8, wherein:
the transfixed multiple dental prosthesis extends along a prosthetic corridor (CP),
said at least one retaining seat extends radially with respect to the first longitudinal axis (II-II) and substantially along the prosthetic corridor (CP).

* * * * *